United States Patent
Bois et al.

(10) Patent No.: US 9,459,245 B2
(45) Date of Patent: Oct. 4, 2016

(54) MEASUREMENT OF PROPERTIES OF SAMPLE OF CURING COMPOSITIONS UNDER HIGH PRESSURE

(75) Inventors: Axel Pierre Bois, Curis Au Mont D'or (FR); Jérémie Saint-Marc, Copenhagen (DK); André Garnier, Montardon (FR); Grégory Galdiolo, Pau (FR); Pierre Illing, Ouffet (FR); Christian Schroeder, Gonrieux (BE)

(73) Assignee: TOTAL S.A., Courbevoie (FR)

( * ) Notice: Subject to any disclaimer, the term of this patent is extended or adjusted under 35 U.S.C. 154(b) by 492 days.

(21) Appl. No.: 13/878,872

(22) PCT Filed: Oct. 11, 2011

(86) PCT No.: PCT/IB2011/054473
§ 371 (c)(1),
(2), (4) Date: Apr. 11, 2013

(87) PCT Pub. No.: WO2012/049620
PCT Pub. Date: Apr. 19, 2012

(65) Prior Publication Data
US 2013/0192382 A1   Aug. 1, 2013

(30) Foreign Application Priority Data
Oct. 12, 2010   (FR) ..................................... 10 58307

(51) Int. Cl.
*G01N 33/38*   (2006.01)
(52) U.S. Cl.
CPC .................................. *G01N 33/383* (2013.01)
(58) Field of Classification Search
CPC ............. G01N 33/381–33/388; G01N 33/442
USPC ..................................................... 73/866, 803
See application file for complete search history.

(56) References Cited

U.S. PATENT DOCUMENTS

| | | | |
|---|---|---|---|
| 4,138,892 A * | 2/1979 | Davis | B28B 7/0044 249/170 |
| 4,259,868 A * | 4/1981 | Rao | G01N 29/07 73/597 |
| 4,377,087 A * | 3/1983 | Rodot | G01N 29/024 73/594 |
| 4,408,489 A * | 10/1983 | Spangle | G01N 33/383 73/866 |

(Continued)

FOREIGN PATENT DOCUMENTS

| WO | WO-2007020435 A1 | 2/2007 |
| WO | WO-2010094925 A1 | 8/2010 |

OTHER PUBLICATIONS

International Preliminary Report on Patentability, IB, Geneva, issued Apr. 16, 2013.

*Primary Examiner* — Lisa Caputo
*Assistant Examiner* — Tran M Tran
(74) *Attorney, Agent, or Firm* — Harness, Dickey & Pierce, P.L.C.

(57) ABSTRACT

A method for testing a curing composition, comprising includes a curing composition; injecting the curing composition into a mold; curing the curing composition into a cured composition, in the mold at a controlled curing pressure; measuring at least one physical or mechanical property of the cured sample at a controlled test pressure, in the mold; the mold being rigid relatively to the cured sample during the curing step.

18 Claims, 3 Drawing Sheets

(56) References Cited

U.S. PATENT DOCUMENTS

| | | | | |
|---|---|---|---|---|
| 4,487,056 A * | 12/1984 | Wiley | G01N 15/0826 | |
| | | | 73/38 | |
| 4,573,342 A * | 3/1986 | Jones | G01N 15/08 | |
| | | | 73/38 | |
| 4,848,145 A * | 7/1989 | Blaschke | E21B 43/267 | |
| | | | 73/152.55 | |
| 5,009,512 A * | 4/1991 | Lessi | G01B 7/16 | |
| | | | 33/557 | |
| 5,159,828 A * | 11/1992 | Steiger | E21B 49/006 | |
| | | | 73/38 | |
| 5,226,310 A * | 7/1993 | Steiger | E21B 49/006 | |
| | | | 73/38 | |
| 5,325,723 A * | 7/1994 | Meadows | G01N 3/10 | |
| | | | 100/106 | |
| 5,571,951 A * | 11/1996 | Jamth | G01N 33/383 | |
| | | | 73/53.01 | |
| 5,836,200 A * | 11/1998 | Belonenko | G01L 9/0022 | |
| | | | 73/24.06 | |
| 5,869,750 A * | 2/1999 | Onan | G01N 3/10 | |
| | | | 73/64.41 | |
| 5,992,223 A * | 11/1999 | Sabins | G01N 29/032 | |
| | | | 73/54.03 | |
| 6,042,760 A * | 3/2000 | Nakazawa | B29C 45/50 | |
| | | | 264/328.1 | |
| 6,112,599 A * | 9/2000 | Maki, Jr. | G01N 29/11 | |
| | | | 73/587 | |
| 6,595,068 B2 * | 7/2003 | Brovold | G01N 3/10 | |
| | | | 73/803 | |
| 6,817,238 B2 * | 11/2004 | Go Boncan | G01N 33/383 | |
| | | | 73/149 | |
| 6,918,292 B2 * | 7/2005 | Go Boncan | G01N 33/383 | |
| | | | 73/149 | |
| 7,089,816 B2 * | 8/2006 | Hakimuddin | G01N 3/00 | |
| | | | 73/865.6 | |
| 7,191,663 B2 * | 3/2007 | Go Boncan | G01N 3/08 | |
| | | | 73/803 | |
| 7,296,927 B2 * | 11/2007 | Reddy | G01N 11/08 | |
| | | | 374/47 | |
| 7,331,242 B2 * | 2/2008 | Kim | G01N 3/60 | |
| | | | 73/766 | |
| 7,364,422 B2 * | 4/2008 | Canossi | B29C 49/4236 | |
| | | | 425/451.6 | |
| 7,380,466 B2 * | 6/2008 | Deeg | G01N 33/383 | |
| | | | 73/803 | |
| 7,549,320 B2 * | 6/2009 | Funkhouser | G01N 3/10 | |
| | | | 73/37 | |
| 7,552,468 B2 * | 6/2009 | Burch | G06Q 40/04 | |
| | | | 705/37 | |
| 7,552,648 B2 * | 6/2009 | McMechan | G01N 3/12 | |
| | | | 73/803 | |
| 7,621,186 B2 * | 11/2009 | Heathman | G01N 3/24 | |
| | | | 73/803 | |
| 8,601,882 B2 * | 12/2013 | Gray | G01N 3/24 | |
| | | | 73/803 | |
| 8,783,091 B2 * | 7/2014 | Meadows | G01N 3/08 | |
| | | | 73/37 | |
| 8,960,013 B2 * | 2/2015 | Meadows | 73/803 | |
| 2003/0204008 A1 * | 10/2003 | Campion | C08K 5/0025 | |
| | | | 524/495 | |
| 2013/0340505 A1 * | 12/2013 | Go Boncan | G01N 33/383 | |
| | | | 73/38 | |

* cited by examiner

MEASUREMENT OF PROPERTIES OF SAMPLE OF CURING COMPOSITIONS UNDER HIGH PRESSURE

CROSS-REFERENCE TO RELATED APPLICATIONS

This application is a National Phase Entry of International Application No. PCT/IB2011/054473, filed on Oct. 11, 2011, which claims priority to French Patent Application Serial No. 1058307, filed on Oct. 12, 2010, both of which are incorporated by reference herein.

FIELD OF THE INVENTION

The present invention relates to a method for testing a curing composition in which one or more parameters of a sample obtained by curing the curing composition under pressure and temperature are measured. The invention relates to a suitable test device for applying a particular embodiment of the above method. The invention in particular applies to curing compositions used in the field of oil extraction, and most particularly to cement compositions for cementation of casings.

BACKGROUND

Cementation of a casing in an oil well consists of placing a sheath of cement in the annular space between the convex side of the casing and the wall of the hole. The hole may be formed with another casing or with the rock. This cement sheath has an essential role in the stability and isolation of oil wells.

The cement sheath is obtained by pumping a cement slurry made from cement, water and adjuvants. This cement slurry is in the liquid state when it is pumped. Hydration of the cement particles leads the liquid slurry towards a solid state, characterized by the existence of a backbone and pores, thereby forming a porous medium.

The cement sheath is exposed to various mechanical and thermal stresses, also called bottom conditions, during the lifetime of the well, from operations conducted in the well (pressure tests, mud changing, cold and hot stimulations, production of reserves . . . ) or from phenomena directly arising in the subsoil (compaction of the reservoir, earthquakes . . . ) and this until it is abandoned, or even beyond this. These stresses may damage the constitutive material of the cement sheath, degrade its mechanical and hydraulic properties and therefore modify its contribution to the stability and seal of the well.

Knowledge of the behavior of the cement under bottom conditions and of the time-dependent change of this behavior is essential for analyzing the operation of the well during its drilling, its exploitation and for guaranteeing its seal for storing and sequestering gas ($CH_4$, $C_2H_6$, $CO_2$, for example) in underground reservoirs. More generally, it is necessary to be able to conduct mechanical or physical tests on materials obtained by curing compositions (and notably cement compositions) under very specific conditions which are those encountered in the wells, i.e. generally absence of air and high pressure. These materials are actually very different from those obtained by curing compositions of the same type under ambient conditions (i.e. in air and under atmospheric pressure).

Many techniques have been proposed for characterizing the mechanical behavior of such materials. A first category of techniques covers static mechanical tests on samples which are cured in ageing benches at a given pressure and temperature, which are then unloaded in order to position them in a measurement apparatus. The unloading step requires bringing back the samples to atmospheric pressure and to room temperature, which may not only damage the samples but also perturb the determination of the characteristics of said samples.

A second category of techniques covers dynamic tests based on indirect measurement of wave propagation and not comprising any return of the samples under ambient conditions. These techniques however have a limited benefit because of their indirect nature: in particular the static parameters have to be obtained from dynamic parameters by using correlation formulae; these formulae are themselves obtained by static tests, which may be marred with errors, or even not cover the field of application of the tested materials. A third category of techniques comprises a few proposals of static mechanical tests without the detrimental unloading and reloading step mentioned above.

Thus, document EP 1541987 describes a system in which a cement composition is cast into a bone-shaped mold, the sample is aged under temperature and under pressure and uniaxial tensile loading is carried out until breakage of the sample, without having to unload the sample. However, with this method, it is not possible to carry out the measurements under bottom conditions, the pressure can only be exerted on both faces of the sample and the other faces are subject to a loading condition by reaction of the mold and not by application of stress under bottom conditions. The measurements are therefore biased. Further, only tensile tests are possible, but the latter are biased as regards the measurement of the elastic constants relatively to the compression tests, because of the occurrence of microcracks which invalidate the elasticity assumption. The range for determining the elastic parameters is therefore highly reduced. Further, it is not possible to measure the breakage parameters in compression and finally the geometry used is unconventional.

Document U.S. Pat. No. 7,621,186 describes an alternative of the previous system, adopting a geometry of the frusto-conical type. It therefore suffers from the same drawbacks. Document WO 2007/020435 proposes a technique which consists of having the cement composition set in an annular space located between two concentric tubes, and of then varying the pressures on the concave side of the inner tube and/or on the convex side of the outer tube while measuring the induced deformations. This technique only allows confinement compression tests (radial direction), and not axial compression tests. Further, this technique has the drawback of being based on a measurement in a heterogeneous field of stresses (in elasticity, the stress and deformation fields in a hollow cylinder vary as $1/r^2$). Thus the measurement of the elastic properties of the sample are highly inaccurate (very sensitive to errors), just like that of the damaging and breakage properties of the sample.

Document U.S. Pat. No. 7,089,816 describes a technique which consists of having the cement composition set in a cylindrical casing (consisting of a deformable membrane and of two pistons) placed in a confinement enclosure, and then of directly proceeding with the mechanical tests by applying the confinement pressure through the membrane and axial loading via the pistons, just like for a conventional triaxial cell. But in reality, the use of a flexible membrane for the setting of the cement does not give the possibility of obtaining a sample with a regular shape after setting. Because of the changes in volume associated with setting, there actually occur Taylor instabilities leading to the sample losing its initial geometry. Also, with this technique it is not possible to carry out measurements in line with the existing procedures, hydration of the cement is not properly reproduced.

Document U.S. Pat. No. 7,549,320 corresponds to a technique of the same type, with a change in the loading technology. In particular, the document further proposes to have the sample set in a flexible membrane. The rigid compartment surrounding the flexible membrane is intended for applying fluids but it does not have an influence on the shape of the sample during the setting.

Document U.S. Pat. No. 7,552,648 further describes another alternative, wherein fluid is injected into the sample itself, which is porous, in order to obtain the desired pressure. A tensile test is then carried out. No compression test is provided, and the provision of an exterior fluid does not properly simulate the hydric exchanges under bottom conditions.

Therefore, there exists a need for having a novel technique for testing cement samples (or other curing compositions) not having the above drawbacks. In particular, there exists a need for having a technique available with which measurements of mechanical, hydraulic or physico-chemical properties may be carried out under bottom conditions during the curing or even beyond this, without again passing through atmospheric temperature and pressure conditions, while controlling the shape of the sample, and without being limited to an unconventional geometry.

SUMMARY

The invention firstly relates to a method for testing a curing composition, comprising:
  providing a curing composition;
  injecting the curing composition into a mold;
  curing the curing composition into a cured sample in the mold, at a controlled curing pressure;
  measuring at least one physical or mechanical property of the cured sample at a controlled test pressure, in the mold;
  the mold being rigid with respect to the cured sample during the curing step.

According to an embodiment, the mold includes a main axis, the curing pressure being controlled by a stress exerted on the sample along the main axis of the mold. According to an embodiment, the mold is also rigid with respect to the cured sample during the measurement step, the mold preferably including a metal wall, and most preferably a stainless steel wall. According to an embodiment, the test pressure is controlled by injecting an internal fluid into the mold and/or by a stress exerted on the sample along the main axis of the mold. According to an embodiment, the mold is flexible relatively to the cured sample during the measurement step.

According to an embodiment, the mold includes a flexible internal jacket and a removable rigid external shell, the external shell being in contact with the internal jacket during the curing step and not being in contact with the internal jacket during the measurement step. According to an embodiment, the test pressure is controlled by injecting an internal fluid into the internal jacket of the mold and/or by a stress exerted on the sample along the main axis of the mold and/or by injecting a confinement fluid into a confinement enclosure surrounding the mold. According to an embodiment, the curing composition is selected from compositions of gels, resins, muds and hydraulic binders, and preferably is a composition comprising water and a hydraulic binder, most preferably a composition comprising water and cement.

According to an embodiment, the mold has the shape of a cylinder. According to an embodiment, the temperature of the sample is regulated during the curing step and/or during the measurement step preferably by maintaining the sample under adiabatic conditions. According to an embodiment, the measurement step comprises one or more measurements selected from acoustic measurements, displacement, pressure, electric resistivity, temperature and permeability measurements and combinations thereof.

The invention also relates to a device for testing a curing composition, comprising:
  a confinement enclosure;
  a mold adapted for receiving a curing composition sample, comprising a main axis, placed in the confinement enclosure and comprising:
    a flexible internal jacket;
    a rigid external shell adapted so as to be flattened against the internal jacket in a removable way;
  first means for compressing the sample by exerting a stress along the main axis of the mold;
  second means for compressing the sample by injecting a confinement fluid into the confinement enclosure around the mold.

According to an embodiment, the device comprises third means for compressing the sample by injecting an internal fluid into the internal case of the mold. According to an embodiment, the mold has the shape of a cylinder. According to an embodiment, the device comprises one or more acoustic sensors, displacement, pressure, electrical resistivity and/or temperature sensors. According to an embodiment, the external shell comprises two, preferably porous, half-shells, and the device comprises a system suitable for separating the half-shells.

With the present invention it is possible to overcome the drawbacks of the state of the art. More particularly it provides a technique with which measurements of properties of a sample may be carried out under bottom conditions during the curing (notably in the case of cement) or beyond this without any step perturbing the unloading, while properly controlling the shape of the sample, and without being limited to unconventional geometry. This is accomplished by using a test device comprising a mold which is rigid during the curing of the sample, provided with means for compressing the sample both for the curing step and for the test step.

According to certain particular embodiments, the invention also has one or preferably several of the advantageous features listed below.
  The rigidity of the mold during the curing step gives the possibility of avoiding deformation of the sample during this step and guarantees that the desired shape is obtained.
  According to a first embodiment, the mold remains rigid during the measurement step. This allows a test of the oedometric type to be carried out (without any radial deformation of the sample). The corresponding device is of small size and easily transportable.
  According to a second embodiment, the mold becomes flexible during the measurement step. This allows a test of the uniaxial or triaxial type to be carried out on the sample, i.e. in which a confinement pressure is applied around the sample.

The temperature of the sample may be regulated during the curing and/or during the measurement. It is also possible to operate under quasi-adiabatic conditions.

With the invention, it is possible to carry out measurements of radial and axial displacements (deformation), permeability measurements, acoustic measurements with compression or shear waves, electrical resistivity measurements, temperature measurements or any other physico-chemical measurement.

With the invention, it is for example possible to test cylindrical samples with a diameter of 50 mm and a height of 100 mm, at a confinement pressure ranging up to 70 MPa and at a temperature ranging up to 150° C.

DETAILED DESCRIPTION

The invention will now be described in more detail and in a non-limiting way in the following description. By curing composition, is meant within the scope of the invention a fluid composition (liquid, slurry, granular composition . . . ) capable of passing to a solid or quasi-solid state over time (by undergoing a curing step). The curing composition may thus be a gel, resin, mud composition or preferably a composition of hydraulic binder and water (with optionally other compounds in the mixture) and more particularly a slag (a composition based on cement and water). Thus, the curing in this case essentially corresponds to hydration (or setting) of the curing composition.

According to the first embodiment of the method of the invention, a rigid mold is used for receiving the curing composition sample. According to the second embodiment of the method of the invention, a flexible mold is used with a removable rigid (preferably porous) shell so as to benefit from a mold which is rigid during the curing of the curing composition and supple (flexible) during the measurement on the cured sample. By "rigid", is meant within the scope of the invention an element which is not capable of deforming (or which is not capable of substantially deforming) under conditions (notably pressure conditions) encountered during the curing step (and for the first embodiment, also during the measurement step). By "flexible" is meant within the scope of the invention a non-rigid element.

Rigid Mold

Figure 1A:
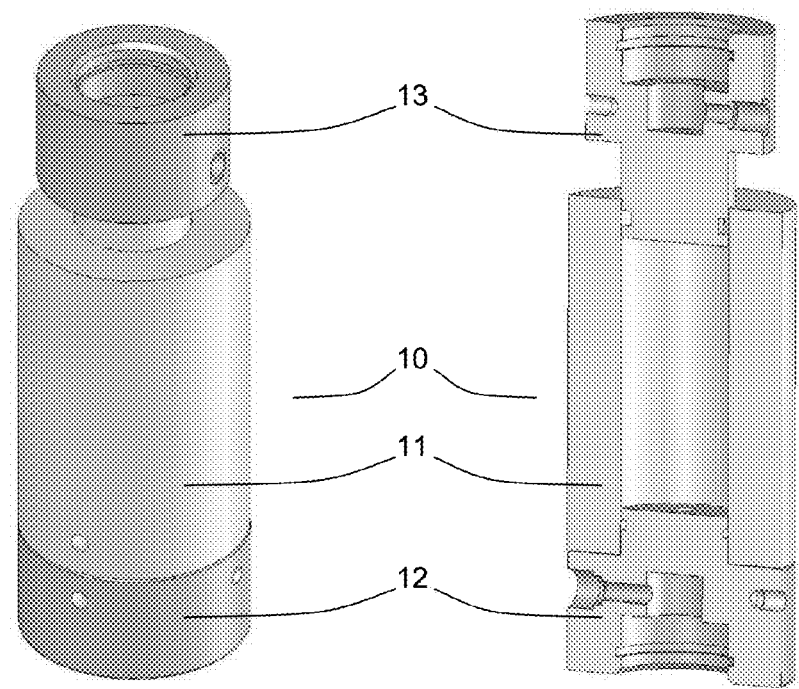
FIG. 1A schematically illustrates a mold used within the scope of the first embodiment of the invention (outer view and sectional view).

With reference to FIG. 1A, the rigid mold 10 used in the first embodiment includes a wall 11 of the tubular type (which delimits a hollow body) as well as an upper base 13 and a lower base 12 at two ends of the wall 11. Preferably, the wall 11 has a main axis, the upper base 13 and the lower base 12 being located at the respective ends of this axis. According to the preferred alternative which is illustrated, the wall 11 is of cylindrical geometry, and the main axis corresponds to the axis of the cylinder. This geometry is a traditional geometry for physical and mechanical measurements on curing compositions, with which it is possible to obtain reliable results and easy to interpret as well as compare.

However it is possible to contemplate other geometries, for example of the frusto-conical type. It is also possible to provide a complementary molding element in the mold 10 in order to obtain a sample, for example a cylindrical sample, having a recess. The wall 11 may be a metal wall and notably a stainless steel wall.

Figure 2:
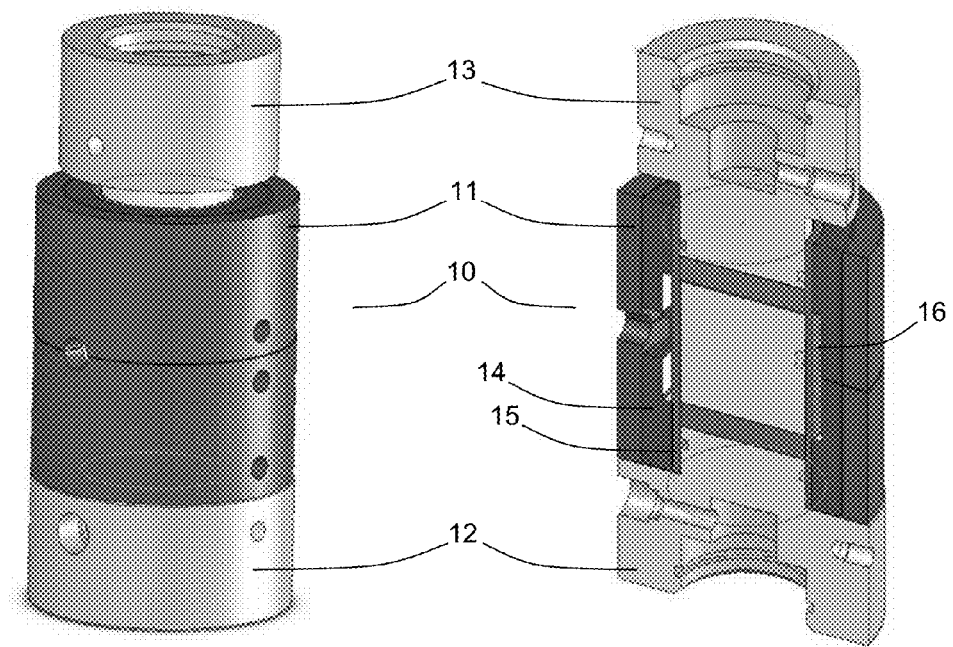
FIG. 2 schematically illustrates an alternative of the mold used within the scope of the first embodiment of the invention (outer view and sectional view).

According to an alternative, it is possible to provide inside the wall 11 an internal layer, for example in plastic material, preferably insulating and heat-stable and notably in polyetherketone (PEEK). With this alternative it is possible to limit the heat exchanges between the inside and the outside of the mold 10. As an example, a cylindrical stainless steel wall 11, with a height of 150 mm, with an external diameter of 100 mm, and an internal diameter of 70 mm and an internal PEEK layer with an external diameter of 70 mm and internal diameter of about 50 mm may be provided. The wall 11 may be simply slid along the internal layer. According to another alternative, which is illustrated in FIG. 2, the hollow body of the mold 10 comprises the wall 11, an internal layer 14 as described above and a heating device inside the internal layer 14, for example comprising a heating collar 16 and a thermal contact layer 15.

In the illustrated example, the thermal contact layer 15 is a brass tube (for example with an internal diameter of about 50 mm and an external diameter of about 56 mm) fitting into the PEEK tube of the internal layer 14 (for example with an internal diameter 56 mm and an external diameter of 70 mm), which itself fits into the stainless steel tube of the wall (for example with an internal diameter of 70 mm and an external diameter of 100 mm). In order to facilitate assembling and dissembling of the mold 10, the wall 11 and the internal layer 14 are each in two portions along the main axis of the mold 10. The heating collar 16 is positioned in a recess made at the junction between both portions. In this alternative, the heat exchanges between the sample and the external medium are limited, while imposing the temperature of the sample: this is a more practical and more accurate temperature control than the one (also possible) consisting of imposing a temperature outside the mold 10, the transmission of heat being effected through the wall 11 of the mold 10.

Figure 1B:
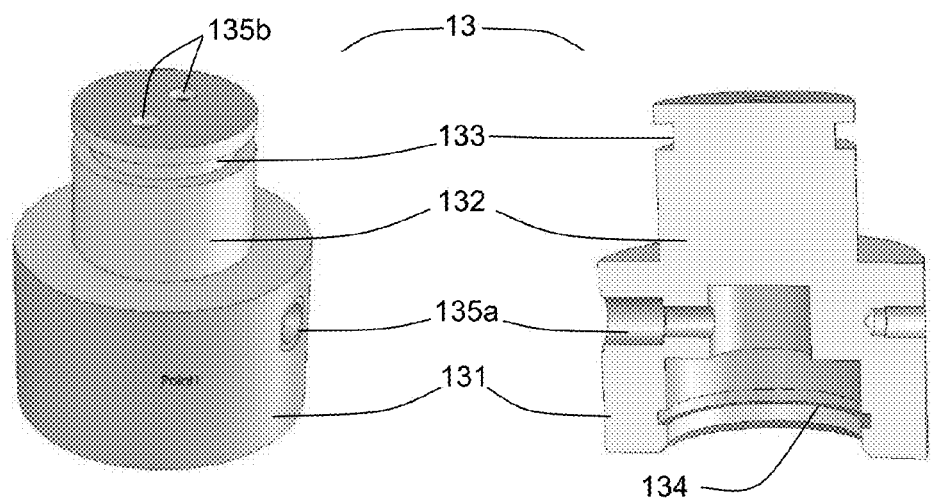
FIGS. 1B and 1C schematically illustrate details of the mold of FIG. 1A (outer view and sectional view).

An embodiment of the upper base 13 is illustrated in FIG. 1B. The upper base 13 comprises a head 131 and a projection 132. The projection 132 is adapted so as to cooperate with the central portion (hollow body) of the mold 10, i.e. sliding in the wall 11 (or possibly in the internal layer 14 or the thermal contact layer 15). It is advantageously provided with a seal gasket 133 (preferably a Quadring® since this is a mobile part).

The head 131 is adapted so as to cooperate with a piston (not shown). A seal gasket 134 (preferably an O-ring) provides the seal with the piston. A hydraulic and electric connection 135a, 135b gives the possibility of providing fluid in the mold 10 as well as the electric power supply of the apparatus.

Figure 1C:
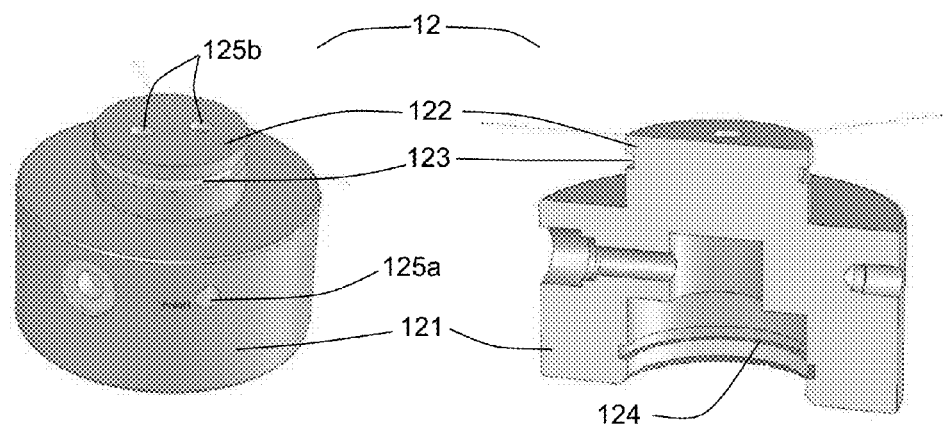

An embodiment of the lower base 12 is illustrated in FIG. 1C. The lower base 12 comprises a head 121 and a projection 122. The projection 122 is adapted so as to cooperate with the central portion (hollow body) of the mold 10 without any sliding. It is advantageously provided with a seal gasket 123 (preferably an O-ring since this is a mobile part).

The head 121 is adapted so as to cooperate with a piston (not shown). A seal gasket 124 (preferably an O-ring)

provides the seal with the piston. With a hydraulic and electric connector 125a, 125b it is possible to ensure circulation of fluid in the mold 10 as well as the electric power supply of the apparatus.

For applying the invention, a curing composition sample is placed in the mold 10 (the upper base 13 being removed during this phase and then positioned when the mold 10 is filled with a curing composition). Next the curing composition sample is set under pressure by means of the piston described above, with which it is possible to exert an axial stress on the sample via upper 13 and lower 12 bases (for example by placing the mold 10 in a press) and thereby impose curing pressure in the mold 10. Also, the temperature of the sample may be regulated during the curing (see for example the alternative of FIG. 2).

The curing pressure and possibly the temperature in the mold 10 may follow a program so as to simulate an injection of curing composition at the well bottom. For example, the pressure of the sample may be high, up to about 20 MPa and the temperature, up to 50-150° C. during the curing. The pressure of the sample is preferably not decreased before the beginning of the measurement phase. In other words, the pressure of the sample between the curing and the measurement preferably remains always greater than or equal to 1 MPa, or 2 MPa, or 3 MPa, or 5 MPa or 10 MPa, or 15 MPa or 20 MPa.

After the curing, the axial stress is modified so as to switch to a test pressure, at which is carried out the measurement of physical or mechanical property(ies) on the cured sample. The test pressure may be greater or lower than the curing pressure, constant or vary over time according to a pre-established program. The same may apply for temperature. The displacement of the upper base 13 allows measurement of the axial deformation of the sample. Complementary sensors, for example pressure, temperature, electrical resistivity or further wave velocity sensors, may be provided inside the mold 10.

It should be noted that the curing of the sample is not necessarily complete (finished) when the measurement is conducted. The measurement may be carried out on a sample which is only partly cured. This first embodiment with a rigid mold gives the possibility of carrying out a measurement under oedometric conditions, i.e. without any radial displacement.

According to an alternative, the test pressure may also be imposed totally or partly by injection of a fluid (a so-called internal fluid) into the mold 10 (by using the hydraulic connectors described above). In this case, the imposed pressure is pore pressure. The injected fluid may be water but also oil, or even a gas, notably an acid gas such as $CO_2$ or $H_2S$, if it is desired to study the behavior of the sample in the presence of such compounds, which are generally present in the well.

According to an alternative, pads are positioned between the projections 122, 132 of the bases 12, 13 and inside the mold 10, in order to create axial isolation between the sample and the bases. These pads are pierced in order to allow hydraulic and electric connections. For example it is possible to use PEEK pads with a thickness of 10 mm. According to an alternative, respective porous stones are positioned between the projections 122, 132 of the bases 12, 13 and the inside of the mold 10, in order to facilitate control of the pore pressure in the sample.

The measurements may be carried out under drained or non-drained conditions. A measurement under drained conditions is carried out at constant pore pressure. A method for carrying out a drained test consists of achieving slow loading, and of leaving the ports open so that the changes in pressure of the pores have time to dissipate. A maximum loading rate depends on the permeability of the tested sample, on the nature of the fluids present in the pores and on the geometry of the sample.

A measurement under non-drained conditions is carried out at non-constant pore pressure. Non-drained loading consists of rapidly loading the sample so that the pore pressures cannot be dissipated. The best method therefore consists of closing all the ports so that the fluid may escape from the sample. Several measurements may be conducted on the sample, by successively or even cyclically loading it. Once the procedure is finished, it is also possible to remove the sample from the mold 10 and to analyze it.

The first embodiment of the invention in particular allows evaluation of the kinetic law for hydrating cement, in particular with the alternative of FIG. 2. It is possible to adjust in real time the temperature inside the mold 10 to the same value as that of the cement during hydration, so as to be under quasi-adiabatic conditions. The temperature measurement then gives information on the amount of released heat. Now, it should be noted that conventional calorimetry systems allowing tracking of the hydration of the cement do not withstand the high pressure conditions of the invention.

Mold with a Flexible Jacket and Removable Rigid Shell

Figure 3:
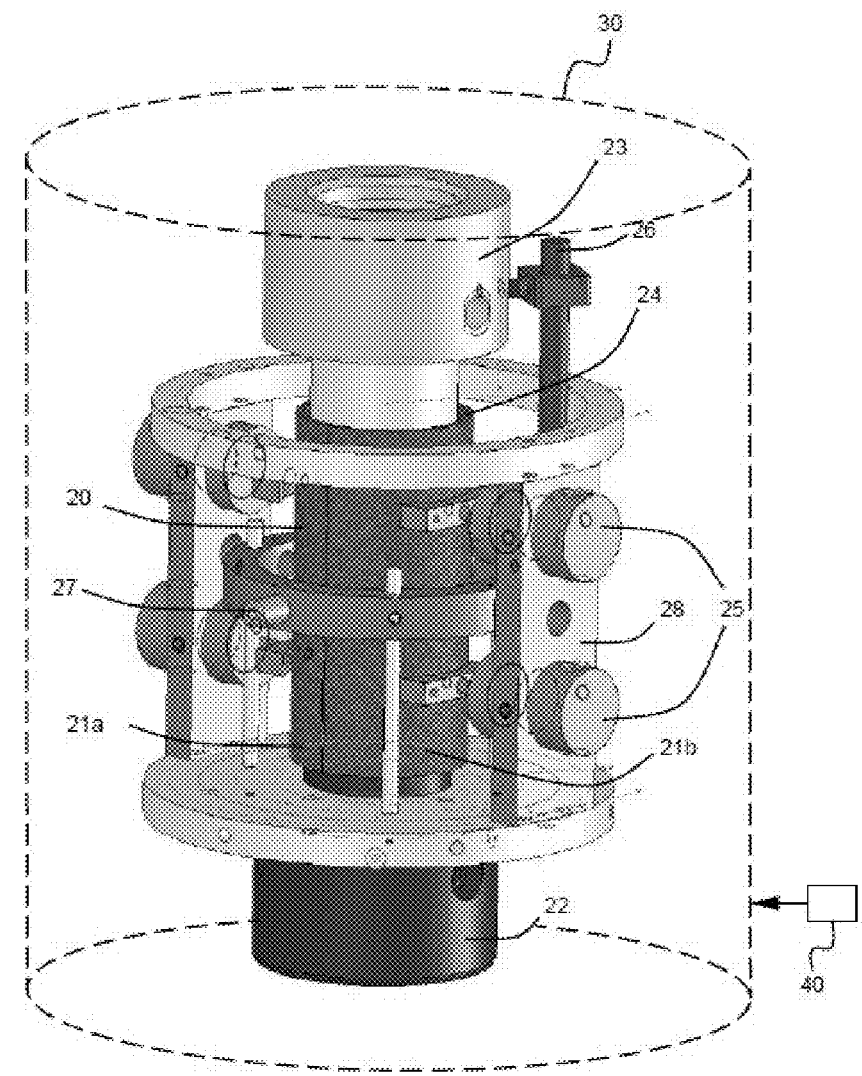
FIG. 3 schematically illustrates a mold used within the scope of the second embodiment of the invention (outer view).

With reference to FIG. 3 the mold 20 used in the second embodiment includes a hollow body as well as an upper base 23 and a lower base 22 at two ends of the hollow body. Preferably, the hollow body has a main axis, the upper base 23 and the lower base 22 being located at the respective ends of this main axis. Just like for the embodiment of the rigid mold, a cylindrical geometry is preferred for the hollow body.

The hollow body comprises a flexible internal (tubular) jacket 24 and a removable rigid external (also tubular) shell 21a, 21b. The rigid external shell is adapted so as to surround and be flattened against (in contact with) the flexible internal jacket 24 over essentially the whole external surface of the latter; and also in order to be removed from the flexible internal jacket 24 when this is desired. In the illustrated alternative, the rigid external shell 21a, 21b is separated into two half-shells, according to a plane comprising the main axis. When the half-shells are closed, the whole of the rigid external shell 21a, 21b is in contact with the flexible internal jacket 24, and when they are open, they are not in contact with the flexible internal jacket 24. Thus, the mold 20 is rigid when the half-shells are closed (because it then consists of the flexible internal jacket 24 and of the rigid external shell 21a, 21b), and it is flexible when the half-shells are open, since it then only comprises the flexible internal jacket 24.

Both half-shells are preferably made in a porous (with fine pores) and rigid material such as sintered metal. This structure ensures both rigidity of the shell and allows transmission of the confinement fluid pressure to the flexible internal jacket 24 surrounding the sample. As a metal, for example copper, brass or steel may be used. The flexible internal jacket 24 may be in, preferably heat-stable, polymeric plastic material. Polytetrafluoroethylene (known under the brand of Teflon®), copolymers of hexafluoropropylene and of vinylidene chloride, terpolymers of tetrafluorethylene, and of vinylidene fluoride and hexafluoropropylene, as well as elastomers containing perfluoromethylvinylether (polymers known under the brand of Viton®) are examples of suitable materials for the flexible internal jacket 24.

The mold 20 is positioned in a confinement enclosure. For example it is possible to use a confinement enclosure 30 for triaxial tests marketed by GL System in Germany. This confinement enclosure is a sealed enclosure provided with means for injecting a fluid 40 (for example oil) with which a control pressure may be imposed in the enclosure 30 (confinement pressure) and notably around the mold 20.

A sample holder (not shown) is positioned in the confinement enclosure 30 in order to support the whole of the mold 20. Hydraulic micro-actuators 25 attached on supports 28 connected to the sample holder allow control of the opening or closing of the half-shells, so as to place or remove the rigid external shell, 21a, 21b.

The upper base 23 and the lower base 22 may be attached to a loading frame (not shown) which allows an axial force to be exerted on the sample in the mold 20. These bases are of a same type as those described above in connection with FIGS. 1B and 1C. They comprise perforations for placing the sensors and for controlling the pore pressure in the sample, and O-rings for ensuring the seal of the system. It is possible to provide a steel head between the upper base 23 and the piston through which the frame exerts the axial stress.

It is possible to provide a basin for recovering materials in the case of a leak. Measurement devices of the same type as those described in connection with the embodiment of the rigid mold are also provided. Further, for the measurement of axial displacements, provision may be made for one or several axial linear variable differential transformers (LVDT) and for the measurement of radial displacements, a radial LVDT 27.

Loading the curing composition sample in the mold 20 is carried out similarly to the embodiment with a rigid mold. The rigid external shell 21a, 21b is flattened against the flexible internal jacket 24, and the curing composition sample is set under pressure by imposing an axial stress on the sample similarly to the embodiment with a rigid mold. The temperature of the sample may be regulated during the curing by heating in the confinement enclosure 30 or else directly in the mold 20.

After the curing, a confinement pressure is applied before removing the rigid external shell 21a, 21b (by opening the half-shells), so that the sample does not again pass through atmospheric pressure before the measurement phase. Preferably, the pressure of the sample remains quasi-constant during the removal of the rigid external shell 21a, 21b, by the application of the confinement pressure. The measurement phase itself is carried out at a test pressure corresponding to a controlled axial stress (similarly to the embodiment with a rigid mold) and/or to a controlled confinement pressure (imposed by the fluid lying in the confinement enclosure 30, to which the flexible internal jacket 24 is impervious) and/or to a controlled pore pressure (similarly to the embodiment with a rigid mold).

The temperature may be controlled during the measurement phase just like during the curing phase. With displacement, pressure, temperature, electric resistivity, wave velocity sensors . . . , it is possible to carry out measurement of the desired parameter(s). This second embodiment allows a measurement of the uniaxial or triaxial type to be carried out. The measurements may be carried out under drained or non-drained conditions and may be repeated successively, or even cyclically, and the sample may be removed and analyzed similarly to the embodiment with a rigid mold.

EXAMPLES

The following examples illustrate the invention without limiting it.

Example 1

First Measurement Procedure (Embodiment of the Rigid Mold)

This procedure may be applied with the embodiment of FIG. 1 or that of FIG. 2.
1. Preparing the measurement cell by:
   a. positioning the body of the cell on its lower base;
   b. making the necessary connections for the measurements (axial displacement, temperature, velocity of compressional and shear waves, electric resistivity, . . . );
   c. placing a heating collar on the outside of the cell.
2. Preparing a volume of cement slag.
3. Filling the measurement cell with cement slag optionally pre-heated.
4. Positioning the upper base above the measurement cell and closing the latter by placing the end of the base having the quad ring inside the body of the cell.
5. Placing the measurement cell under a press or any other device with which an axial force may be applied.
6. Applying an axial stress ramp as well as a temperature ramp in order to reach the bottom conditions. Once these conditions are reached, the pressure and temperature remain constant.
7. Carrying out at any moment before, during or after the setting of the cement, loading cycles with:
   a. axial stress;
   b. pore pressure;
   c. temperature.
8. Measurement of the consequences of these loading cycles in terms of:
   a. axial deformation of the sample;
   b. pore pressure;
   c. temperature;
   d. velocity of compressional and shear waves;
   e. electric resistivity.
9. Once the test is finished, disassembling the specimen and observing the cement sample.

This measurement procedure allows measurement of the following parameters, at any moment during the setting of the cement:
  elastic oedometric modulus of the cement under drained or non-drained conditions;
  plastic oedometric modulus of the cement under drained or non-drained conditions;
  plasticity onset stress of the cement under drained or non-drained conditions;
  creeping properties of the cement;
  velocity of compressional waves of the cement under drained or non drained conditions;
  velocity of shear waves of the cement under drained or non-drained conditions;
  electric resistivity of the cement under drained or non-drained conditions;
  thermal expansion coefficient of the cement under drained or non-drained conditions
  permeability of the cement.

Example 2

Second Measurement Procedure (Embodiment of the Rigid Mold)

This procedure relates to tests of the maturometry type. It may be performed on an alternative as illustrated in FIG. 2.

1. Preparing the measurement cell by:
   a. positioning the body of the cell on its lower base;
   b. making the necessary connections for the measurements (axial displacement, temperature, velocity of compressional and shear waves, electric resistivity, . . . )
2. Preparing a volume of cement slag.
3. Filling the measurement cell with the optionally preheated cement slag.
4. Positioning the upper base above the measurement cell and closing the latter by placing the end of the base having the quadring inside the body of the cell.
5. Placing the measurement cell under a press or any other device with which an axial force may be applied.
6. Applying an axial stress ramp as well as a temperature ramp in order to reach the bottom conditions. Once these conditions are reached, the pressure remains constant.
7. During the setting, applying a set temperature value such that the temperature of the heating collar located between the PEEK cylinder and the copper cylinder is always equal to the temperature of the cement, a temperature measured by means of measurement sensors such as thermocouples.
8. Performing at any moment, before, during or after the setting of the cement of loading cycles with
   a. axial stress;
   b. pore pressure;
   c. temperature.
9. Measurement of the consequences of these loading cycles in terms of:
   a. axial deformation of the sample;
   b. pore pressure;
   c. temperature;
   d. velocity of compressional and shear wave;
   e. electric resistivity.
10. Once the test is finished, disassembling the specimen and observing the cement sample.

With this measurement procedure it is possible to measure in addition to the parameters accessible according to the first measurement procedure, the amount of heat from hydration of the cement versus progression of the chemical reactions.

Example 3

Third Measurement Procedure (Embodiment with a Flexible Jacket and Rigid Shell

This procedure may be applied with the embodiment of FIG. 3.
1. Preparing the measurement cell by:
   a. mounting the lower base on the sample holder;
   b. positioning the flexible Viton® or Teflon® flexible jacket on the lower base.
   c. closing both half-shells around the flexible jacket;
   d. making the necessary connections for the measurements (axial displacement, temperature, velocity of compressional and shear waves, electric resistivity, . . . ).
2. Preparing a volume of cement slag.
3. Filling the area comprised inside the flexible jacket with optionally pre-heated cement slag,
4. Positioning the upper base above the measurement cell and closing the area containing the cement slag by placing the end of the base inside the flexible jacket.
5. Placing the head on the upper base.
6. Inserting the sample holder (with the device, object of the invention) in a confinement enclosure with which a confinement pressure may be applied (via a confinement fluid). This confinement enclosure is equipped with heating devices. A piston is positioned above the head of the cell. It emerges from the confinement enclosure.
7. Placing the confinement enclosure under a press or any other device with which an axial force may be applied.
8. Applying an axial stress ramp and confinement pressure as well as a temperature ramp in order to reach the bottom conditions. Once these conditions are reached, the pressure and temperature remain constant.
9. Opening at any moment after the setting of the cement, both half-shells with which it is thereby possible to obtain a cement sample with a cylindrical shape, positioned in the flexible jacket, on which a fluid pressure is applied, a configuration similar to the one encountered during a standard triaxial test.
10. Performing loading/unloading cycles according to what is practiced during standard triaxial tests;
    a. isotropic stress path: the axial stress variation is equal to that of the radial stress;
    b. triaxial stress path: the variation of radial stress is zero;
    c. proportional stress path: the axial stress variation is proportional to that of the radial stress;
    d. oedometric stress path: the variation of radial displacement is zero;
    e. stress path by controlling the pore pressure;
    f. stress path by controlling the temperature.
11. Measurement of the consequences of these loading cycles in terms of:
    a. axial deformation of the sample;
    b. radial deformation of the sample;
    c. pore pressure;
    d. temperature;
    e. velocity of compressional and shear wave;
    f. electric resistivity . . . .
12. Once the test is finished, disassembling the specimen and observing the cement sample.

With this measurement procedure it is possible to measure the following parameters:
elastic properties (Young's, shear, incompressibility, oedometric, moduli, Poisson coefficient) of the cement under drained or non-drained conditions;
plastic properties (axial, transverse deformability) of the cement under drained or non-drained conditions;
poro-mechanical coupling properties of the cement (Biot coefficient, Skempton coefficient . . . );
creeping properties of the cement;
plasticity onset stress of the cement under drained or non-drained conditions;
velocity of compressional waves of the cement under drained or non-drained conditions;
velocity of shear waves of the cement under drained or non-drained conditions;
electric resistivity of the cement under drained or non-drained conditions;
thermoexpansion coefficient of the cement under drained or non-drained conditions;
permeability of the cement . . . .

The invention claimed is:
1. A method for testing a curing composition, the method comprising:
   (a) providing a curing composition;
   (b) injecting the curing composition into a hollow body of a mold so that the curing composition contacts the hollow body, the hollow body having a main axis and comprising:
      a flexible internal layer radially deformable to the main axis when subjected to a controlled test pressure; and a rigid external wall adapted to be in contact with the flexible internal layer in a removable way;
(c) curing the curing composition into a cured sample, in the mold, at a controlled curing pressure;
(d) wherein the flexible internal layer is not capable of deforming radially to the main axis when subjected to the controlled curing pressure during the curing step due to the support of the rigid internal wall;
(e) removing the rigid external wall; and
(f) measuring at least one physical or mechanical property of the cured sample at a controlled test pressure, in the mold.

2. The method according to claim 1, wherein the mold includes a main axis, further comprising controlling the curing pressure by a stress exerted on the sample along the main axis of the mold.

3. The method according to claim 1, wherein the hollow body of the mold includes a stainless steel wall.

4. The method according to claim 2, further comprising controlling the test pressure through at least one of: (a) by injecting an internal fluid into the mold, and (b) by a stress exerted on the sample along the main axis of the mold.

5. The method according to claim 1, wherein the curing composition is selected from compositions of gels, resins, muds and hydraulic binders.

6. The method according to claim 1, wherein the mold is of cylindrical shape.

7. The method according to claim 1, further comprising regulating the temperature of the sample during at least one of: (a) the curing step, and (b) the measurement step, by maintaining the sample under adiabatic conditions.

8. The method according to claim 1, wherein the measurement step comprises at least one measurement selected from acoustic, displacement, pressure, electric resistivity, temperature, permeability measurements and combinations thereof.

9. The method according to claim 1, further comprising controlling the test pressure by at least one of: (a) injecting an internal fluid into the internal jacket of the mold, (b) a stress exerted on the sample along the main axis of the mold, and (c) injecting a confinement fluid into a confinement enclosure surrounding the mold.

10. The method according to claim 1, further comprising inserting acid gas into the mold containing the curing composition sample.

11. A device for testing a curing composition, the device comprising:
(a) a confinement enclosure;
(b) a mold adapted to receive a curing composition sample within a hollow body, the mold being positioned in the confinement enclosure, the hollow body having a main axis and comprising:
a flexible internal jacket adapted to radially deform to the main axis when subjected to a controlled test pressure; and
a rigid external shell adapted to be in contact with the flexible internal jacket in a removable way so that the flexible internal layer is not capable of deforming radially to the main axis when subjected to a controlled curing pressure during curing due to the support of the rigid external wall;
(c) an upper base and a lower base for compressing the sample by exerting a stress along the main axis of the mold, the upper and lower bases being located at two ends of the hollow body with respect to the main axis; and
(d) a confinement fluid injector for compressing the sample by injecting a confinement fluid into the confinement enclosure around the mold.

12. The device according to claim 11, wherein the upper base or the lower base comprises a connector for compressing the sample by injecting, via the connector, an internal fluid into the internal jacket of the mold.

13. The device according to claim 11, wherein the mold is of a cylindrical shape.

14. The device according to claim 11, comprising at least one acoustic, displacement, pressure, electric resistivity and/or temperature sensor.

15. The device according to claim 11, wherein the external shell comprises two half-shells which are porous, the device further comprising at least one actuator operably separating the half-shells.

16. The device according to claim 11, wherein the curing composition sample is oil well casing cement.

17. The device according to claim 11, wherein acid gas is inserted into the mold containing the curing composition sample.

18. The method according to claim 1, wherein the curing composition sample is oil well casing cement.

* * * * *